United States Patent [19]

Brändström et al.

[11] Patent Number: 5,441,968
[45] Date of Patent: * Aug. 15, 1995

[54] THERAPEUTICALLY ACTIVE FLUORO SUBSTITUTED BENZIMIDAZOLES

[75] Inventors: Arne E. Brändström, Göteborg; Per L. Lindberg, Askim; Gunnel E. Sundén, Göteborg, all of Sweden

[73] Assignee: Aktiebolaget Hässle, Mölndal, Sweden

[*] Notice: The portion of the term of this patent subsequent to Dec. 28, 2010 has been disclaimed.

[21] Appl. No.: 134,255
[22] Filed: Oct. 8, 1993

Related U.S. Application Data

[62] Division of Ser. No. 596,984, Dec. 7, 1990, Pat. No. 5,274,099, which is a division of Ser. No. 454,048, Dec. 20, 1990, Pat. No. 5,049,674.

[51] Int. Cl.⁶ .................. C07D 401/12; A61K 31/44
[52] U.S. Cl. .................................... 514/338; 546/271
[58] Field of Search ......................... 546/271; 546/338

[56] References Cited

U.S. PATENT DOCUMENTS

| | | | |
|---|---|---|---|
| 4,182,766 | 1/1980 | Krasso | 546/271 |
| 4,255,431 | 3/1981 | Junggren | 546/271 |
| 4,337,252 | 6/1982 | Junggren | 546/271 |
| 4,359,465 | 11/1982 | Ruwant | 546/271 |
| 4,508,905 | 4/1985 | Junggren | 546/271 |
| 4,555,518 | 11/1985 | Rainer | 546/271 |
| 4,599,347 | 7/1986 | Krasso | 546/271 |
| 4,628,098 | 12/1986 | Nohara | 546/271 |
| 4,727,150 | 2/1988 | Nohara | 546/271 |
| 4,738,974 | 4/1988 | Brändström | 546/271 |
| 4,738,975 | 4/1988 | Nohara | 546/271 |
| 4,965,269 | 10/1990 | Brändström | 546/271 |
| 5,021,433 | 6/1991 | Alminger et al. | 546/271 |
| 5,021,433 | 6/1991 | Alminger et al. | 546/271 |
| 5,215,974 | 6/1993 | Alminger et al. | 546/271 |

FOREIGN PATENT DOCUMENTS

| | | |
|---|---|---|
| 167943 | 7/1984 | European Pat. Off. |
| 176308 | 4/1986 | European Pat. Off. |
| 221041 | 5/1987 | European Pat. Off. |
| 268953 | 6/1988 | European Pat. Off. |
| 279149 | 8/1988 | European Pat. Off. |
| 295603 | 12/1988 | European Pat. Off. |
| 1500043 | 2/1978 | United Kingdom |
| 1525958 | 9/1978 | United Kingdom |

OTHER PUBLICATIONS

Derwent 87-294449/42, 1987.

Primary Examiner—Jane Fan
Attorney, Agent, or Firm—White & Case

[57] ABSTRACT

The novel compounds of the formulas I and I'

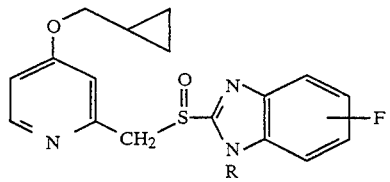

wherein F is in 5 or 6 position and

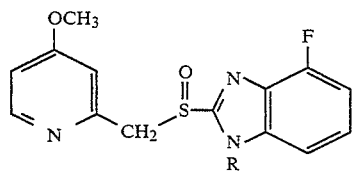

wherein in both formulas R is the group —CH$_2$OCOOR$^1$, wherein R$^1$ is a straight or branched alkyl containing 1–6 carbon atoms or benzyl, or R$^1$ is the group

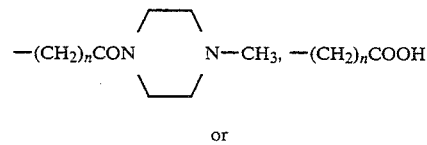

or

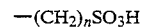

wherein n is 1–6 and physiologically acceptable salts thereof as well as intermediates, pharmaceutical compositions containing such compounds as active ingredient, and the use of the compounds in medicine.

5 Claims, No Drawings

THERAPEUTICALLY ACTIVE FLUORO SUBSTITUTED BENZIMIDAZOLES

This application is a divisional of application Ser. No. 07/596,984, filed on Dec. 7, 1990, (Issued as U.S. Pat. No. 5,274,099) which in turn is a divisional of application Ser. No. 07/454,048, filed Dec. 20, 1989 (Issued as U.S. Pat. No. 5,049,674 on Sep. 17, 1991).

FIELD OF THE INVENTION

The object of the present invention is to provide novel compounds, and therapeutically acceptable salts thereof, which inhibit exogenously or endogenously stimulated gastric acid secretion and thus can be used in the prevention and treatment of peptic ulcer.

The present invention also relates to the use of the compounds of the invention and therapeutically acceptable salts thereof, for inhibiting gastric acid secretion in mammals including man. In a more general sense, the compounds of the invention may be used for prevention and treatment of gastrointestinal inflammatory diseases, and gastric acid-related diseases in mammals including man, such as gastritis, gastric ulcer, duodenal ulcer, reflux esophagitis, and Zollinger-Ellison syndrome. Furthermore, the compounds may be used for treatment of other gastrointestinal disorders where gastric antisecretory effect is desirable e.g. in patients with gastrinomas, and in patients with acute upper gastrointestinal bleeding. They may also be used in patients in intensive care situations, and pre- and postoperatively to prevent acid aspiration and stress ulceration. The compounds of the invention may also be used for treatment or prophylaxis of inflammatory conditions in mammals, including man, especially those involving lysozymal enzymes. Conditions that may be specifically mentioned are rheumatoid arthritis and gout. The compounds may also be useful in the treatment of diseases related to bone metabolism disorders as well as the treatment of glaucoma. The invention also relates to pharmaceutical compositions containing the compounds of the invention, or a therapeutically acceptable salt thereof, as active ingredient. In a further aspect, the invention relates to processes for preparation of such new compounds to novel intermediates in the preparation of the compounds and to the use of the active compounds for the preparation of pharmaceutical compositions for the medical use indicated above.

It is a specific primary object of the invention to provide compounds with a high level of bioavailability. The compounds of the invention will also exhibit high chemical stability at neutral and acidic pH and high potency in regard to inhibition of gastric acid secretion. Bioavailability is defined as the fraction or, percent, of the administered dose of compound that is absorbed unchanged into the systemic blood. Potency is in this application defined as the ED$_{50}$ value.

PRIOR ART AND BACKGROUND OF THE INVENTION

Benzimidazole derivatives intended for inhibiting gastric acid secretion are disclosed in numerous patent documents. Among these can be mentioned GB 1 500 043, GB 1 525 958, U.S. Pat. Nos. 4,182,766, 4,255 431, 4,599,347, 4,555,518, 4,727,150, 4,628,098, EP 124 495, EP 208 452, EP 221 041, EP 279 149, EP 176 308 and Derwent abstract 87-294449/42. Benzimidazole derivatives proposed for use in the treatment or prevention of special gastrointestinal inflammatory diseases are disclosed in U.S. Pat. No. 4,539,465.

THE INVENTION

Compounds described in the prior art, as described above, are effective acid secretion inhibitors, and are thus useful as antiulcer drugs. In order to further enhance the usefulness of this type of compounds, a higher bioavailability has been desired, but still the compounds should have a high potency in inhibiting gastric acid secretion and also a high chemical stability at neutral pH.

It has been recognized that 2-[(pyridinylmethyl)sulfinyl]-1H-benzimidazoles tested show a great variability in bioavailability as well as in potency and stability, and it is difficult to identify compounds possessing all the three advantageous properties. There is no guidance in the prior art on how to obtain compounds with this combination of properties.

It has been found that the compounds of the invention, which contain a stability-enhancing, and enzymatically clearable, group (group R in the following formulas) show exceedingly high bioavailability, and still the compounds are very effective as inhibitors of gastric acid secretion and exhibit high chemical stability in solution at neutral and acidic pH. The high chemical stability also at acidic pH, makes the compounds useful for non-enteric coated peroral formulations.

The compounds of the invention are

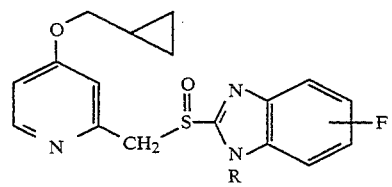

wherein F is in 5 or 6 position and

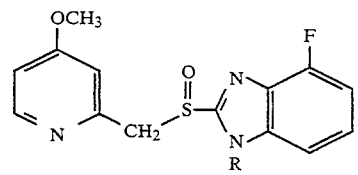

wherein in both formulas R is the group —CH$_2$OCOOR$^1$, wherein R$^1$ is a straight or branched alkyl containing 1–6 carbon atoms or benzyl, or R$^1$ is the group

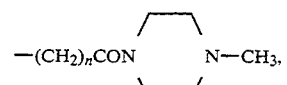

—(CH$_2$)$_n$COOH or —(CH$_2$)$_n$SO$_3$H wherein n is 1–6 as well as physiologically acceptable salts and whereby the group R$^1$ when containing an amino function may be in the form of an ammonium salt having a physiologically acceptable counter anion and when containing a carboxylic acid or sulfonic acid group may be in the form of a salt containing a physiologically acceptable counter cation.

Preferred compounds are 4-fluoro-2-[[(4-methoxy-2-pyridinyl)methyl]sulfinyl-1H-benzimidazole-1-ylmethyl ethyl carbonate, and 5-fluoro and 6-fluoro-2-[[(4-cyclopropyl-methoxy-2-pyridinyl)methyl]sulfinyl]-1H-benzimidazole-1-ylmethyl ethyl carbonate.

Examples of acid-addition salts of the amino function are those from mineral acids, such as HCl, HBr, $H_2SO_4$, $H_3PO_4$ etc. or from mono-, di- or tribasic-carboxylic acids, such as acetic acid, tartaric acid or citric acid. Examples of counter cations of the carboxylic or sulfonic acid in the form of a salt are $Na^+$, $K^+$ or $N^+(R^2)_4$, where $R^2$ is (1–4 C) alkyl.

The compounds of the invention have an asymmetric centre in the sulfur atom, i.e. exists as two optical isomers (enantiomers). Both the pure enantiomers, racemic mixtures (50% of each enantiomer) and unequal mixtures of the two are within the scope of the present invention. Also intermediate compounds and process for the preparation are within the scope. The 5-fluoro and 6-fluoro isomers of the invention, may be used separately, or in equal or unequal mixtures.

PREPARATION

The compounds of the invention may be prepared according to the following methods:

a) Reacting a compound of the formula II or II'

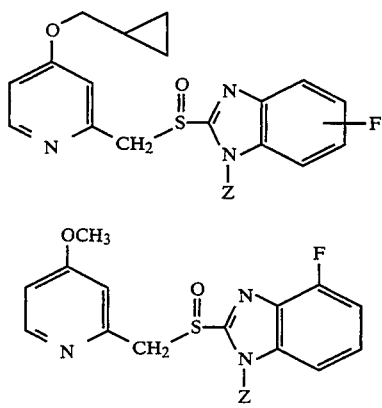

wherein Z is either a metal cation such as $Na^+$, $K^+$, $Li^+$ or $Ag^+$ or a quaternary ammonium ion, such as tetrabutylammonium with alkyl chloromethyl carbonate or benzyl chloromethyl carbonate.

b) Reacting a compound of the formula II or II', wherein Z is hydroxymethyl with a compound of the formula III,

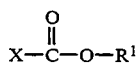

wherein $R^1$ is as defined above and X is Cl or imidazole or p-nitrophenoxy or a functionally equivalent group, in the presence of a suitable base such as triethylamine or 4-N,N-dimethylaminopyridine.

The reactions according to a) and b) are suitably carried out under protective gas in absence of water. Suitable solvents are hydrocarbons such as toluene or benzene or halogenated hydrocarbons such as methylene chloride or chloroform. The reactions may be carried out at a temperature between the ambient temperature and the boiling temperature of the reaction mixture.

c) Hydrolysis of an ester in the $R^1$ substituent in a compound of the formula I or formula I' when containing a carboxyalkyl group protected as an ester.

Depending on the process conditions and the starting materials, the end products of the formula I and I' are obtained either in neutral or salt form. Acid addition salts of the amino-containing compounds may in a manner known per se, be transformed into free base using basic agents such as alkali or by ion exchange. The free bases obtained may then be converted into salts with organic or inorganic acids. Base addition salts of the carboxylic acid-containing compounds may in a corresponding way be transformed into the acid form, and then reconverted to a therapeutically suitable salt such as sodium or potassium salts. The 5-fluoro- and 6-fluoro isomers obtained, may be separated by means of crystallization or chromatography. Racemates obtained can be separated into the pure enantiomers. This may be done according to known methods, e.g. from racemic diastereomeric salts by means of chromatography or fractional crystallization.

Intermediates of the formula II and II' utilized in the method a) may be obtained according to processes known per se, as is exemplified below.

Alkyl chloromethyl carbonate and benzyl chloromethyl carbonate may be obtained from the pertinent alcohol by treatment with chloromethyl chloroformate in the presence of pyridine.

Intermediates of the formula II and II' wherein Z is hydroxymethyl are obtained by reaction of the corresponding benzimidazole compound carrying H in the N-—1 position with formaldehyde, as is exemplified below. Starting materials of the formula III may be obtained by known methods, e.g. from an alcohol $HOR^1$ by treatment with phosgene or $1,1^1$-carbonyl-diimidazole or p-nitrophenyl chloroformate.

Intermediates utilized in the method c) may be obtained according to the method b) wherein $R^1$ contains a carboxyalkyl group protected as an ester.

The starting materials described in the intermediate examples, may be obtained according to processes known per se.

For clinical use a compound of the invention is formulated into pharmaceutical formulations for oral, rectal, parenteral or other modes of administration. The pharmaceutical formulation contains a compound of the invention normally in combination with a pharmaceutically acceptable carrier. The carrier may be in the form of a solid, semi-solid or liquid diluent, or a capsule. These pharmaceutical preparations are a further object of the invention. Usually the amount of active compound is between 0.1–95% by weight of the preparation, between 0.2–20% by weight in preparations for parenteral use and between 1–50% by weight in preparations for oral administration.

In the preparation of pharmaceutical formulations containing a compound of the present invention in the form of dosage units for oral administration a compound selected may be mixed with a solid, powdered carrier, such as lactose, saccharose, sorbitol, mannitol, starch, amylopectin, cellulose derivatives, gelatin, or another suitable carrier, stabilizing substances such as alkaline compounds e.g. carbonates, hydroxides and oxides of sodium, potassium, calcium, magnesium and the like, as well as with lubricating agents such as magnesium stearate, calcium stearate, sodium stearyl fumarate and polyethylenglycol waxes. The mixture is then processed into granules or pressed into tablets. Granules and tablets may be coated with an enteric coating which protects the active compound from acid catalyzed degradation as long as the dosage form remains in the stomach. The enteric coating is chosen among pharmaceutically acceptable enteric-coating materials e.g. beeswax, shellac or anionic film-forming polymers such as cellulose acetate phthalate, hydroxypropyl-methylcellulose phthalate, partly methyl esterified methacrylic acid polymers and the like, if preferred in combination with a suitable plasticizer. To the coating various dyes may be added in order to distinguish among tablets or granules with different active compounds or with different amounts of the active compound present.

Soft gelatine capsules may be prepared with capsules containing a mixture of an active compound of the invention, vegetable oil, fat, or other suitable vehicle for soft gelatine capsules. Soft gelatine capsules may also be enteric-coated as described above. Hard gelatine capsules may contain granules or enteric-coated granules of the active compound. Hard gelatine capsules may also contain the active compound in combination with a solid powdered carrier such as lactose, saccharose, sorbitol, mannitol, potato starch amylopection, cellulose derivatives or gelatine. The hard gelatine capsules may be enteric-coated as described above.

Dosage units for rectal administration may be prepared in the form of suppositories which contain an active substance mixed with a neutral fat base, or they may be prepared in the form of a gelatine rectal capsule which contains the active substance in a mixture with a vegetable oil, paraffin oil or other suitable vehicle for gelatine rectal capsules, or they may be prepared in the form of a ready-made micro enema, or they may be prepared in the form of a dry micro enema formulation to be reconstituted in a suitable solvent just prior to administration.

Liquid preparation for oral administration may be prepared in the form of syrups or suspensions, e.g. solutions or suspensions containing from 0.2% to 20% by weight of the active ingredient and the remainder consisting of sugar or sugar alcohols and a mixture of ethanol, water, glycerol, propylene glycol and/or polyethylene glycol. If desired, such liquid preparations may contain colouring agents, flavouring agents, saccharine and carboxymethyl cellulose or other thickening agents. Liquid preparations for oral administration may also be prepared in the form of a dry powder to be reconstituted with a suitable solvent prior to use.

Solutions for parenteral administration may be prepared as a solution of a compound of the invention in a pharmaceutically acceptable solvent, preferably in a concentration from 0.1% to 10% by weight. These solutions may also contain stabilizing agents and/or buffering agents and may be manufactured in different unit dose ampoules or vials. Solutions for parenteral administration may also be prepared as a dry preparation to be reconstituted with a suitable solvent extemporaneously before use.

The typical daily dose of the active substance will depend on various factors such as for example the individual requirement of each patient, the route of administration and the disease. In general, oral and parenteral dosages will be in the range of 5 to 500 mg per day of active substance.

The invention is illustrated by the following examples.

EXAMPLE 1

Preparation of 4-fluoro-2-[[(4-methoxy-2-pyridinyl)methyl]sulfinyl]-1H-benzimidazole-1-ylmethyl benzyl carbonate 4-Fluoro-2-[[(4-methoxy-2-pyridinyl)methyl]sulfinyl]-1H-benzimidazole (200 mg, 0.66 mmol) dissolved in methylene chloride (10 ml) was stirred vigorously with an aqueous 5M formaldehyde solution (1 ml, 5 mmol) for three minutes. After separation the organic layer was dried over $MgSO_4$ and filtered. Triethyl amine (0.091 ml, 0.66 mmol) was added to the mixture and a solution of benzyl chloroformate (0.10 ml, 0.66 mmol) 90% pure in methylene chloride (1 ml) was added dropwise. The mixture was stirred 1 h at room temperature and the solution was evaporated. The crude material was purified on silica gel with methylene chloride-ethyl acetate (3:1) as eluent and the product was crystallized from ethanol giving the title compound (yield 0.047 g, 15%). The identity of the title compound obtained was confirmed with NMR. NMR data for the product is given below

EXAMPLE 2

Preparation of 4-fluoro-2-[[(4-methoxy-2-pyridinyl)methyl]sulfinyl]-1H-benzimidazole-1-ylmethyl ethyl carbonate To NaOH (0.26 g, 6.5 mmol) dissolved in $H_2O$ (12 ml) 4-fluoro-2-[[(4-methoxy-2-pyridinyl)methyl]sulfinyl]-1H-benzimidazole (1.0 g, 3.3 mmol) and tetrabutylammoniumhydrogen sulfate (1.1 g, 3.2 mmol) were added under stirring. The mixture was stirred for about 5 min, at ambient temperature and then extracted 3 times with $CH_2Cl_2$ (20 ml). After separation the combined $CH_2Cl_2$ phases were dried over $Na_2SO_4$, filtrated and the solvent evaporated off giving an oil. The residual oil was dissolved in toluene (30 ml). Chloromethyl ethyl carbonate (0.68 g, crude material) dissolved in dry toluene (3 ml) was added under a protective gas and under stirring. The mixture was stirred at ambient temperature over night. The toluene was evaporated off and the residual oil was chromatographed on a silica column using ethyl acetate as eluent. Crystallizing from ethyl acetate-diethyl ether gave the title compound (0.33 g, 25%). NMR data for the product is given below.

EXAMPLE 3 and EXAMPLE 4

Preparation of 5-fluoro-2-[[(4-cyclopropylmethoxy-2-pyridinyl)methyl]sulfinyl]-1H-benzimidazole-1-ylmethyl ethyl carbonate and 6-fluoro-2-[[(4-cyclopropylmethoxy-2-pyridinyl)methyl]sulfinyl]-1H-benzimidazole-1-ylmethyl ethyl carbonate To a mixture of 1-hydroxymethyl-5-fluoro-2-[[(4-cyclopropylmethoxy-2-pyridinyl)methyl]sulfinyl]-1H-benzimidzole and 1-hydroxymethyl-6-fluoro-2-[[(4-cyclopropylmethoxy-2-pyridinyl)methyl]sulfinyl]-1H-benzimidazole, crude material (0.55 g, 1.2 mmol) 80% pure, in methylene chloride (10 ml) were added in the following order, triethyl amine (0.20 ml, 1.4 mmol) and ethyl chloroformate (0.14 ml, 1.5 mmol) dissolved in methylene chloride (4 ml). After stirring the mixture at ambient temperature for one hour under a protective gas, the methylene chloride was evaporated off. The residual oil was chromatographed on a silica column using ethyl actate as eluent. In this way the desired compounds were obtained as an isomeric mixture (ratio 1:1), (0.12 g, 18%). NMR data for the products are given below.

TABLE 1

| Ex. | Solvent | NMR data δ ppm |
|---|---|---|
| 1 | CDCl₃ (300 MHz) | 3.73(s, 3H), 4.34(d, 1H), 4.39(d, 1H), 5.17(s, 2H), 6.46(s, 2H), 6.72(dd, 1H), 6.85(d, 1H), 7.03–7.11(m, 1H), 7.30–7.44(m, 7H), 8.35(d, 1H) |
| 2 | CDCl₃ (300 MHz) | 1.30(t, 3H), 3.80(s, 3H), 4.20(q, 2H), 4.90(s, 2H), 6.40–6.50(m, 2H), 6.75(dd, 1H), 6.90(d, 1H), 7.05–7.15(m, 1H), 7.35–7.40(m, 1H), 7.40–7.45(m, 1H), 8.40(d, 1H) |
| 3 and 4 | CDCl₃ (300 MHz) | 0.30(m, 2H), 0.60–0.65(m, 2H), 1.20(m, 1H), 1.30(m, 3H), 3.65–3.80(m, 2H), 4.20(m, 2H), 4.80(s, 2H), 6.30–6.45(m, 2H), 6.70(dd, 1H), 6.75(d, 1H), 7.10–7.20(m, 1H), 7.35(dd, 0.5), 7.50(dd, 0.5H), 7.60(dd, 0.5H), 7.75(dd, 0.5H), 8.35(d, 1H) |

PREPARATION OF INTERMEDIATES

Example I1 preparation of 4-fluoro-2-[[(4-methoxy-2-pyridinyl)methyl]sulfinyl]-1H-benzimidazole 4-Fluoro-2-[[(4-methoxy-2-pyridinyl)methyl]thio]-1H-benzimidazole (1.31 g, 0.0045 mol) was dissolved in methylene chloride (60 ml). NaHCO₃ (0.76 g, 0.0090 mol) dissolved in water (10 ml) was added and the mixture was cooled to +2° C. m-Chloroperbenzoic acid, 84% (1.64 g, 0.0045 mol) dissolved in methylene chloride (10 ml) was added dropwise with stirring. Stirring was continued at +2° C. for 15 min. After separation the organic layer was extracted with an aqueous 0.20M NaOH solution (2×25 ml, 0.010 mol). The combined aqueous solutions were neutralized to pH 7–8 with 0.1M HCl in the presence of methylene chloride (100 ml). After separation the aqueous layer was extracted with methylene chloride and the combined organic solutions were dried over MgSO₄. The solutions was evaporated and the title compound was obtained (1.06 g, 77%). NMR data for the final product is given below.

EXAMPLE I2 and EXAMPLE I3

Preparation of 1-hydroxymethyl-5-fluoro-2-[[(4-cyclopropylmethoxy-2-pyridinyl)methyl]sulfinyl]-1H-benzimidazole and 1-hydroxymethyl-6-fluoro-2-[[(4-cyclopropylmethoxy-2-pyridinyl)methyl]sulfinyl]-1H-benzimidazole 5-fluoro-2-[[(4-cyclopropylmethoxy-2-pyridinyl)methyl]sulfinyl]-1H-benzimidazole (3.45 g, 10.0 mm was dissolved in methylene chloride (50 ml). A solution of formaldehyde (5M, 10 ml, 50 mmol) was added and the mixture was stirred violently for 2 minutes. The phases were separated and the methylene chloride solution was dried (sodium sulfate), filtered and the solvent was evaporated off at low temperature (<30° C.). The residue, an isomeric mixture (ratio 1:1), 80% pure of the title compounds was used without purification in the subsequent reaction. NMR data for the products are given below.

EXAMPLE I4

Preparation of 1-hydroxymethyl-4-fluoro-2-[(4-methoxy-2-pyridinyl)-methyl]sulfinyl]-1H-benzimidazole 4-Fluoro-2-[[(4-methoxy-2-pyridinyl)methyl]sulfinyl]-1H-benzimidazole (1.6 g, 5.2 mmol) was suspended in methylene chloride (50 ml). Methanol was added until a clear solution was obtained. The mixture was concentrated on a rotavapor under reduced pressure. The oily residue, which was not allowed to crystallize, was dissolved in methylene chloride (30 ml). A solution of formaldehyde (5M, 10 ml, 50 mmol) was added and the mixture was stirred violently for four minutes. After separation the organic solution was dried (Na₂SO₄) and concentrated until 10 ml of the mixture was left. The flask was chilled for 15 minutes whereupon the formed precipitate was filtered off and washed with cold methylene chloride. In this way the title compound was obtained (1.1 g, 63%). NMR data is given below.

EXAMPLE I5

Preparation of 4-cyclopropylmethoxy-2-methylpyridine-N-oxide

To sodium hydride (55% pure) (4.4 g, 0.1 mol) (washed with petroleum ether), cyclopropyl-methanol (50 ml) was added. Then a solution of 2-methyl-4-nitropyridine-N-oxide (6.5 g, 0.042 mol) in cyclopropylmethanol (30 ml) was added during about 1 h. The dark brown mixture was heated to 90° C. and stirred at 90° C. for about 1 h. Thereafter the cyclopropylmethanol was distilled off under reduced pressure and methylene chloride (100 ml) was added to the residue. The mixture was stirred for about 30 minutes, then filtered and concentrated which gave 9.5 g of crude material.

The crude material was purified by flash chromatography on silica with methylene chloride-methanol (90-10) as eluent, giving 4.0 g (53%) of pure title compound. NMR data is given below. EXAMPLE I6

Preparation of 2-acetoxymethyl-4-cyclopropylmethoxypyridine 4-cyclopropylmethoxy-2-methylpyridine-N-oxide (3.8 g 0.021 mol) was dissolved in acetic anhydride (10 ml) and was added dropwise to acetic anhydride (20 ml) (warmed to 90° C.). After the addition the temperature was raised to 110° C. and the mixture was stirred at 110° C. for 1 h and then the solvent was distilled off and the crude product was used without purification. NMR data is given below.

EXAMPLE I7

Preparation of 4-cyclopropylmethoxy-2-hydroxymethylpyridine

To the crude 2-acetoxymethyl-4-cyclopropylmethoxy pyridine, NaOH (100 ml 2M) was added and the mixture was refluxed for 2 hours. The mixture was extracted with methylene chloride, and the phases were separated. The organic layer was dried with Na₂SO₄, filtered and the solvent was evaporated off, yielding 2.7 g of crude title compound. NMR data is given below. The crude product was used without any further purification.

EXAMPLE I8

Preparation of 4-cyclopropylmethoxy-2-chloromethylpyridine hydrochloride 4-cyclopropylmethoxy-2-hydroxymethylpyridine (93% pure) (0.9 g 0.0046 mol) was dissolved in methylene chloride (10 ml) and cooled to 0° C. $SOCl_2$ (0.5 ml, 0.0069 mol) in methylene chloride (5 ml) was added dropwise at 0° C. and the reaction mixture was stirred 15 min at room temperature. Isopropanol (0.5 ml) was added and the mixture was evaporated giving the desired product (0.68 g, 78%). NMR data is given below.

EXAMPLE I9

Preparation of 5-fluoro-2-[[(4-cyclopropylmethoxy-2-pyridinyl)methyl)thio]-1H-benzimidazole To 5-fluoro-2-mercapto-1H-benzimidazole (0.88 g, 0.0051 mol) in methanol (25 ml) NaOH (0.2 g, 0.0051 mol) dissolved in $H_2O$ (1 ml) and 4-cyclopropylmethoxy-2-chloromethylpyridine hydrochloride (0.91 g, 0.0046 mol) dissolved in methanol (10 ml) were added in the given order. The mixture was heated to boiling and NaOH (0.2 g, 0.005 mol) dissolved in $H_2O$ (1 ml) was added and the mixture was refluxed for 1 hour. After evaporation of methanol, $CH_2Cl_2$ (75 ml) and $H_2O$ (50 ml) were added and pH adjusted to 10. The mixture was vigorously stirred, the phases were separated, the organic phase was dried over $Na_2SO_4$ and evaporated giving the desired product (1.25 g, 72%). NMR data for the product is given below.

EXAMPLE I10

Preparation of 4-fluoro-2-mercapto-1H-benzimidazole 1,2-diamino-3-fluorobenzene (1.6 g, 12.7 mmol) and potassium ethyl xanthogenate (2.64 g, 16.5 mmol) were dissolved in ethanol (25 ml) and water (6 ml). The mixture was refluxed for 14 hours and then concentrated on a rotavapor. Water (20 ml) was added and the solution was acidified with 2M hydrochloric acid. The precipitate was filtered off and dried. In this way the title compound was obtained (1.23 g, 58%). NMR is given below.

EXAMPLE I11

Preparation of 4-fluoro-2-[[(4-methoxy-2-pyridinyl)methyl]thio]-1H-benzimidazole To a solution of 4-fluoro-2-mercapto-1H-benzimidazole (1.15 g, 0.0068 mol) in methanol (60 ml) NaOH (0.54 g, 0.014 mol) dissolved in water (3 ml) and 4-methoxy-2-chloromethylpyridine hydrochloride (1.32 g, 0.0068 mol) dissolved in methanol (20 ml) were added in the given order. The mixture was refluxed for one hour whereupon the solution was evaporated. The residue was partitioned between methylene chloride and water. After separation the organic solution was dried over $MgSO_4$ and evaporated giving an oil which was purified on silica gel (50 g) using 1% methanol in methylene chloride as eluent. In this way the title compound was obtained (1.35 g, 69%). NMR data for the product is given below.

Example I12

Preparation of 5-fluoro-2-[[(4-cyclopropylmethoxy-2-pyridinyl)methyl]sulfinyl]-1H-benzimidazole 5-Fluoro-2-[[(4-cyclopropylmethoxy-2-pyridinyl)methyl]thio]-1H-benzimidazole (1.25 g, 0.0036 mol) was dissolved in $CH_2Cl_2$ (40 ml). $NaHCO_3$ (0.6 g, 0.0072 mol) dissolved in $H_2O$ (20 ml) was added and the mixture was cooled to +2° C. m-Chloroperbenzoic acid, 84% (0.73 g, 0.0036 mol) dissolved in $CH_2Cl_2$ (5 ml) was added under stirring. Stirring was continued at room temperature for 15 min. The two phases were separated and NaOH (0.29 g, 0.0072 mol) dissolved in $H_2O$ (25 ml) was added to the organic phase. The mixture was stirred, the phases were separated and the $H_2O$ phase was treated with Norite and filtered. Methylformiate (0.45 ml, 0.0073 mol) dissolved in $H_2O$ (5 ml) was added dropwise under stirring. After extraction with $CH_2Cl_2$ and drying with $Na_2SO_4$ the solvent was evaporated. In this way the title compound was obtained (0.93 g, 69%). NMR data for the final product is given below.

NMR data for the intermediates are given below.

TABLE 2

| Ex. | Solvent | NMR data δ ppm |
|---|---|---|
| I1 | $CDCl_3$ (500 MHz) | 3.65(s, 3H), 4.55(d, 1H), 4.75(d, 1H) 6.65(d, 1H), 6.75(dd, 1H), 7.05(dd, 1H), 7.25(dt, 1H), 7.3–7.4(b, 1H), 8.35(d, 1H) |
| I2 and I3 | $CDCl_3$ (500 MHz) | 0.30(m, 2H), 0.65(m, 2H), 1.20(m, 1H), 3.60–3.80(m, 2H), 4.70(m, 1H), 4.80(m, 1H), 5.55(m, 1H), 5.90(m, 1H), 6.70(m, 1H), 6.75(m, 1H), 7.05–7.10(m, 0.5H), 7.15–7.20(m, 0.5H), 7.20(dd, 0.5H), 7.40(dd, 0.5H), 7.50(dd, 0.5H), 7.70(dd, 0.5H), 8.15(d, 1H) |
| I4 | DMSO (300 MHz) | 3.74(s, 3H), 4.76(d, 1H), 4.89(d, 1H), 5.7–5.9(m, 2H), 6.91(dd, 1H), 7.00(d, 1H), 7.1–7.2(m, 1H), 7.40(m, 1H), 7.60(d, 1H), 8.33(d, 1H) |
| I5 | $CDCl_3$ (500 MHz) | 0.36(m, 2H); 0.68(m, 2H); 1.26(m, 1H); 2.52(s, 3H); 3.83(d, 2H); 6.70(dd, 1H); 6.77(d, 1H); 8.16(d, 1H) |
| I6 | $CDCl_3$ (500 MHz) | 0.37(m, 2H); 0.69(m, 2H); 2.16(s, 3H); 3.87(d, 2H); 6.75(dd, 1H); 6.87(d, 1H); 8.42(d, 1H) |
| I7 | $CDCl_3$ (500 MHz) | 0.36(m, 2H); 0.67(m, 2H); 1.27(m, 1H); 3.86(d, 2H); 4.69(s, 2H); 6.72(dd, 1H); 6.78(d, 1H); 8.33(d, 1H) |
| I8 | DMSO (300 MHz) | 0.40(m, 2H); 0.60(m, 2H); 1.30(m, 1H); 4.20(d, 2H); 5.00(s, 2H); 7.45(dd, 1H); 7.65(d, 1H); 8.70(d, 1H) |
| I9 | $CDCl_3$ (500 MHz) | 0.36–0.39(m, 2H); 0.67–0.71(m, 2H); 1.27(m, 1H); 3.89(d, 2H), 4.29(s, 2H); 6.81(dd, 1H); 6.89(d, 1H); 6.94(m, 1H); 7.24(dd, 1H); 7.46(dd, 1H), 8.43(d, 1H) |
| I10 | DMSO (500 MHz) | 6.95(d, 1H), 7.00(dd, 1H), 7.10(dt, 1H) |
| I11 | $CDCl_3$ (500 MHz) | 3.90(s, 3H), 4.30(s, 2H), 6.85(dd, 1H), 6.90(d, 1H), 6.90(dd, 1H), 7.10(dt, 1H), 7.2–7.4(b, 1H), 8.50(d, 1H) |
| I12 | $CDCl_3$ (500 MHz) | 0.22(m, 2H); 0.60(m, 2H); 1.10(m, 1H); 3.45(m, 1H); 3.60(m, 1H); 4.52(d, 1H); 4.70(d, 1H); 6.65(d, 1H); 6.70(dd, 1H); 7.08(m, 1H); 7.30–7.90(b, 2H); 8.28(d, 1H) |

The best mode of carrying out the invention known at present is to use the compound described in Example 3 and 4.

Pharmaceutical preparations containing a compound of the invention as active ingredient are illustrated in the following formulations.

Syrup

A syrup containing 1% (weight per volume) of active substance was prepared from the following ingredients:

| | |
|---|---|
| The compound according to Example 1 | 1.0 g |
| Sugar, powder | 30.0 g |
| Saccharine | 0.6 g |
| Glycerol | 5.0 g |
| Tween | 1.0 g |
| Flavouring agent | 0.05 g |
| Ethanol 96% | 5.0 g |
| Distilled water q.s. to a final volume of | 100 ml |

A solution of the compound according to Example 1 in ethanol and Tween was prepared. Sugar and saccharine were dissolved in 60 g of warm water. After cooling the solution of the active compound was added to the sugar solution and glycerol and a solution of flavouring agents dissolved in ethanol were added. The mixture was diluted with water to a final volume of 100 ml.

Tablets

A tablet containing 50 mg of active compound was prepared from the following ingredients:

| | | | |
|---|---|---|---|
| I | Compound according to Example 1 | 500 g | |
| | Lactose | 700 g | |
| | Methyl cellulose | 6 g | |
| | Polyvinylpyrrolidone cross-linked | 50 g | |
| | Magnesium stearate | 15 g | |
| | Sodium carbonate | 6 g | |
| | Distilled water | q.s. | |
| II | Hydroxypropyl methylcellulose | 36 g | |
| | Polyethylene glycol | 9 g | |
| | Colour Titanium dioxide | 4 g | |
| | Purified water | 313 g | |

I Compound according to example 1, powder, was mixed with lactose and granulated with a water solution of methyl cellulose and sodium carbonate. The wet mass was forced through a sieve and the granulate dried in an oven. After drying the granulate was mixed with polyvinylpyrrolidone and magnesium stearate. The dry mixture was pressed into tablet cores (10 000 tablets), each tablet containing 50 mg of active substance, in a tabletting machine using 7 mm diameter punches.

II A solution of hydroxypropyl methylcellulose and polyethylene glycol in purified water was prepared. After dispersion of titanium dioxide the solution was sprayed onto the tablets I in an Accela Cota®, Manesty coating equipment. A final tablet weight of 125 mg was obtained.

Solution for intravenous administration

A parenteral formulation for intravenous use, containing 4 mg of active compound per ml, is prepared from the following ingredients:

| | |
|---|---|
| A soluble active compound or compound mixture according to the present invention | 4 g |
| Polyethylene glycol | 400 g |
| Ethanol | 100 g |
| Sterile water to a final volume of | 1000 ml |

The active compound or compound mixture is dissolved in polyethylene glycol and ethanol and sterile water is added to a final volume of 1000 ml. The solution is filtered through a 0.22 μm filter and immediately dispensed into 10 ml sterile ampoules. The ampoules are sealed.

Capsules

Capsules containing 30 mg of active compound were prepared from the following ingredients:

| | |
|---|---|
| A compound mixture according to Examples 3 and 4 | 300 g |
| Lactose | 700 g |
| Microcrystalline cellulose | 40 g |
| Hydroxypropyl cellulose low-substituted | 62 g |
| Purified water | q.s. |

The active compound mixture was mixed with the dry ingredients and granulated with a solution of disodium hydrogen phosphate. The wet mass was forced through an extruder and spheronized and dried in a fluidized bed dryer.

500 g of the pellets above were first coated with a solution of hydroxypropyl methylcellulose, 30 g, in water, 600 g, using a fluidized bed coater. After drying, the pellets were coated with a second coating as given below:

Coating solution

| | |
|---|---|
| Hydroxypropyl methylcellulose phthalate | 70 g |
| Cetyl alcohol | 4 g |
| Acetone | 600 g |
| Ethanol | 200 g |

The final coated pellets were filled into capsules.

Suppositories

Suppositories were prepared from the following ingredients using a welding procedure. Each suppository contained 40 mg of active compound.

Compound according to Example 2 4 g
Witepsol H-15 180 g

The active compound was homogenously mixed with Witepsol H-15 at a temperature of 41° C. The molten mass was volume filled into pre-fabricated suppository packages to a net weight of 1.84 g. After cooling the packages were heat sealed. Each suppository contained 40 mg of active compound.

Biological Effects
Bioavailability
Choice of Species for Testing.

The results from tests on two different animal species, rat and dog, vary in regard to measured level of bioavailability for the same compound. We believe that the rat is the more relevant species for bioavailability testing. This is based on our belief that, the liver metabolism has the most predominant impact upon bioavailability, and the liver metabolic pattern in man for this type of compounds is quite similar to that of the male rat (more so than of the female rat and the dog). Moreover, test results of bioavailability in the male rat will tend to give a broader "spread" compared with the test results in the dog, and thus the male rat model will give more clear differences in bioavailability between different compounds. Stated in another way, the bioavailability as tested in the male rat can be expected to give a better estimate of the relative differences in man between different test compounds compared with the test results obtained when using the same compound in the dog.

Assessment of Bioavailability

Bioavailability, is assessed by calculating the quotient between the areas under plasma concentration (AUC) curve of the compound without a stability-enhancing and enzymatically cleavable group, that is formula I or I' wherein R is replaced by hydrogen (herein defined as compound A), following 1) intraduodenal (id) administration of the corresponding compound according to the invention and 2) intravenous (iv) administration of compound A, from the rat and the dog. Low, therapeutically relevant doses, were used. This method is scientifically recognized as valid for assessing bioavailability (see for instance: M. Rowland and T. N. Tozer, Clinical Pharmacokinetics, 2nd ed., Lea & Febiger, London 1989, p 42). Data are provided in Table 3.

Potency

The potency for inhibition of acid secretion is measured in the male rat and the dog, both intravenously and intraduodenally. When it comes to relevance of the animal test data for potency of a given compound in man for the present type of compounds, it is believed that potency in man will correspond to a level somewhere between what is measured in the male rat and what is measured in the dog. Potency data is provided in Table 3.

Biological Tests

Inhibition of Gastric Acid Secretion in the Conscious Male Rat.

Male rats of the Sprague-Dawley strain are used. They are equipped with cannulated fistulae in the stomach (lumen) and the upper part of the duodenum, for collection of gastric secretions and administration of test substances, respectively. A fourteen days recovery period after surgery is allowed before testing is commenced.

Before secretory tests, the animals are deprived of food but not water for 20 h. The stomach is repeatedly washed through the gastric cannula, and 6 ml of Ringer-Glucose given s.c. Acid secretion is stimulated with infusion during 3.5 h (1.2 ml/h, s.c. ) of pentagastrin and carbachol (20 and 110 nmol/kg h, respectively), during which time gastric secretions are collected in 30-min fractions. Test substances or vehicle are given iv or id at 90 min after starting the stimulation, in a volume of 1 ml/kg. Gastric juice samples are titrated to pH 7.0 with NaOH, 0.1 mol/L, and acid output is calculated as the product of titrant volume and concentration. Further calculations are based on group mean responses from 4–5 rats. The acid output during the periods after administration of test substances or vehicle are expressed as fractional responses, setting the acid output in the 30-min period preceding administration to 1.0. Percentage inhibition is calculated from the fractional responses elicited by test compound and vehicle. $ED_{50}$ values are obtained from graphical interpolation on log dose-response curves, or estimated from single-dose experiments assuming a similar slope for all dose-response curves. The results are based on gastric acid secretion during the second hour after drug/vehicle administration.

Bioavailability in the Male Rat

Male adult rats of the Sprague-Dawley strain were used. One day, prior to the experiments, all rats were prepared by cannulation of the left carotid artery under anaesthesia. The rats used for the intravenous experiments, were also cannulated in the jugular vein. (Ref. V Popovic and P Popovic, J Appl Physiol 1960;15, 727–728). The rats used for the intraduodenal experiments, were also cannulated in the upper part of the duodenum. The cannulas were exteriorized at the nape of the neck. The rats were housed individually after surgery and were deprived of food, but not water, before administration of the test substances. The same dose (4 $\mu$mol/kg) were given iv and id as a bolus for about one minute (2 ml/kg).

Blood samples (0.1–0.4 g) were drawn repeatedly from the carotid artery at intervals up to 4 hours after given dose. The samples were frozen as soon as possible until analysis of the test compound.

The area under the blood concentration vs time curve, AUC, for the compound A, determined by the linear trapezoidal rule and extrapolated to infinity by dividing the last determined blood concentration by he elimination rate constant in the terminal phase. The systemic bioavailability (F %) of the compound A following intraduodenal administration of compounds of the invention of formula I was calculated as $$F(\%) = \frac{AUC \text{ (Compound A)}_{id(compound\ of\ the\ invention)}}{AUC \text{ (Compound A)}_{iv(Compound\ A)}} \times 100$$

Inhibition of Gastric Acid Secretion and Bioavailability in the Conscious Dog

Harrier dogs of either sex were used. They were equipped with a duodenal fistula for the administration of test compounds or vehicle and a cannulated ventricular fistula for the collection of gastric secretions.

Before secretory tests the animals were fasted for about 18 h but water was freely allowed. Gastric acid secretion was stimulated by a 4 h infusion of histamine dihydrochloride (12 ml/h) at a dose producing about 80% of the individual maximal secretory response, and gastric juice collected in consecutive 30-min fractions. Test substance or vehicle was given id or iv 1 h after starting the histamine infusion, in a volume of 0.5 ml/kg body weight. The acidity of the gastric juice samples were determined by titration to pH 7.0, and the acid output calculated. The acid output in the collection periods after administration of test substance or vehicle were expressed as fractional responses, setting the acid output in the fraction preceding administration to 1.0. Percentage inhibition was calculated from fractional responses elicited by test compound and vehicle. $ED_{50}$ values were obtained by graphical interpolation on log dose-response curves, or estimated from single-dose experiments under the assumption of the same slope of the dose-response curve for all test compounds. All results reported are based on acid output 2 h after dosing.

Blood samples for the analysis of test compound concentration in plasma were taken at intervals up to 3 h after dosing. Plasma was separated and frozen within 30 min after collection and later analyzed AUC (area under the plasma concentration-time curve) for compound A, extrapolated to infinite time, was calculated by the linear trapezoidal rule. The systemic bioavailability (F %) of the compound A after id administration of compounds of the invention was calculated as described above in the rat model.

Chemical Stability

The chemical stability of the compounds of the invention has been followed kinetically at low concentration at 37° C. in aqueous buffer solution at different pH values. The results in Table 3 show the half life (t ½) at pH 7, that is the time period after which half the amount of the original compound remains unchanged, and $t_{10\%}$ at pH 2, that is the time period after which 10% of the original compound has decomposed.

Results of biological and stability tests

Table 3 gives a summary of the test data available for the compounds of the invention.

TABLE 3

Biological Test Data and Stability Data

| Test compound Example no. | Inhibition of acid secretion id administration $ED_{50}$ μmol/kg | | Bio- availability F % | | Chemical Stability at | |
|---|---|---|---|---|---|---|
| | Dog | Rat | Dog | Rat | pH 7 t½ (h) | pH2 t 10% (h) |
| 1 | — | — | — | — | — | 2 |
| 2 | 1.3<sup>a)</sup> | — | 67 | 149 | 16 | 3 |
| 3 and 4 | 2.0 | — | 77<sup>b)</sup> | — | 21 | 5 |

<sup>a)</sup>Dog 1  1.5 μmol/kg - 55%
Dog 2  1.5 μmol/kg no effect
$ED_{50}$ value is based on one dog.
<sup>b)</sup>The value estimated from one dog

We claim:

1. A compound of the formula I

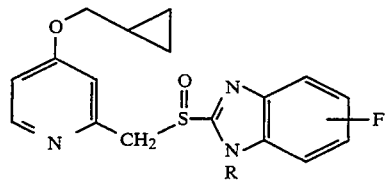

wherein F is in 5 or 6 position and
wherein R is the group —CH$_2$OCOOR$^1$,
wherein R$^1$ is a straight or branched alkyl containing 1–6 carbon atoms or benzyl,
and physiologically acceptable salts thereof.

2. A compound according to claim 1 in the form of its hydrochloride.

3. A pharmaceutical composition containing as active ingredient an effective amount of a compound according to claim 1.

4. A method for inhibiting gastric acid secretion by administering to mammals including man a compound as defined in claim 1.

5. A method for the treatment of gastrointestinal inflammatory diseases in mammals including man by administering a compound as defined in claim 1.

* * * * *